(12) United States Patent
Hirose et al.

(10) Patent No.: US 8,308,297 B2
(45) Date of Patent: Nov. 13, 2012

(54) CONNECTION ADAPTER, OPTICAL TOMOGRAPHIC IMAGING APPARATUS, PROGRAM FOR EXECUTING IMAGING METHOD AND MEMORY DEVICE FOR THE PROGRAM

(75) Inventors: Futoshi Hirose, Yokohama (JP); Yasuyuki Numajiri, Kawasaki (JP); Shuichi Kobayashi, Yokohama (JP); Kenji Muto, Fujisawa (JP); Hirofuni Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 519 days.

(21) Appl. No.: 12/603,144

(22) Filed: Oct. 21, 2009

(65) Prior Publication Data

US 2010/0103374 A1   Apr. 29, 2010

(30) Foreign Application Priority Data

Oct. 24, 2008 (JP) .................................. 2008-273880
Oct. 19, 2009 (JP) .................................. 2009-240891

(51) Int. Cl.
*A61B 3/14* (2006.01)

(52) U.S. Cl. ........................................ 351/206; 351/221

(58) Field of Classification Search .................. 351/206, 351/205, 200, 221, 246
See application file for complete search history.

(56) References Cited

U.S. PATENT DOCUMENTS

| | | | |
|---|---|---|---|
| 4,830,483 A | 5/1989 | Kohayakawa et al. | |
| 4,866,243 A | 9/1989 | Sakane et al. | |
| 5,537,162 A | 7/1996 | Hellmuth et al. | |
| 5,847,806 A | 12/1998 | Mihashi | |
| 5,894,337 A | 4/1999 | Okinishi et al. | |
| 6,192,269 B1 | 2/2001 | Okumura et al. | |
| 6,324,420 B1 | 11/2001 | Kishida et al. | |
| 6,337,993 B1 | 1/2002 | Kishida et al. | |
| 6,454,722 B1 | 9/2002 | Numajiri et al. | |
| 6,699,198 B2 | 3/2004 | Numajiri | |
| 6,826,359 B1 | 11/2004 | Takeda | |

(Continued)

FOREIGN PATENT DOCUMENTS

EP   1 952 755   6/2008

(Continued)

OTHER PUBLICATIONS

Notification of Reason for Refusal, dated Nov. 9, 2010, issued by the Japanese Patent Office in Japanese Application No. 2009-240891.

(Continued)

*Primary Examiner* — Hung Dang
(74) *Attorney, Agent, or Firm* — Fitzpatrick, Cella, Harper & Scinto (57) ABSTRACT

A connection adapter constituting an optical tomographic imaging apparatus has a small installation space and high use efficiency. The connection adapter is disposed between a fundus camera main body portion and a camera portion to be attached to the fundus camera main body portion for imaging a surface image of a fundus as an object in an optical tomographic imaging apparatus, and connects them in a detachable manner. The connection adapter includes: a first light guide unit for guiding tomographic image measuring beams guided from the fundus camera main body portion for imaging the tomographic image to a tomographic imaging portion; and a second light guide unit for guiding fundus image measuring beams guided from the fundus camera main body portion for imaging the surface image of the fundus to the camera portion.

20 Claims, 7 Drawing Sheets

U.S. PATENT DOCUMENTS

| | | |
|---|---|---|
| 6,834,202 B2 | 12/2004 | Ono |
| 7,566,128 B2 | 7/2009 | Tsukada et al. |
| 8,096,658 B2 * | 1/2012 | Kikawa et al. ............... 351/206 |
| 2007/0070295 A1 | 3/2007 | Tsukada et al. |
| 2007/0159595 A1 | 7/2007 | Fukuma et al. |
| 2009/0091766 A1 | 4/2009 | Hirose |
| 2009/0285354 A1 | 11/2009 | Hirose et al. |

FOREIGN PATENT DOCUMENTS

| | | |
|---|---|---|
| EP | 1 952 755 | 8/2008 |
| JP | 08-024222 A | 1/1996 |
| JP | 08-098813 A | 4/1996 |
| JP | 10-033484 A | 2/1998 |
| JP | 2000-107134 A | 4/2000 |
| JP | 2006-212153 A | 8/2006 |
| JP | 2007-181631 | 7/2007 |
| WO | 97/36537 | 10/1997 |
| WO | 2008/115060 | 9/2008 |

OTHER PUBLICATIONS

Notification of the First Office Action dated Jul. 26, 2011, in counterpart Chinese Application No. 200910207030.9.

Aug. 13, 2012 European Official Action in European Patent Appln. No. 09173901.1.

* cited by examiner

CONNECTION ADAPTER, OPTICAL TOMOGRAPHIC IMAGING APPARATUS, PROGRAM FOR EXECUTING IMAGING METHOD AND MEMORY DEVICE FOR THE PROGRAM

BACKGROUND OF THE INVENTION

1. Field of the Invention

The present invention relates to a connection adapter, an optical tomographic imaging apparatus, a program for executing an imaging method and a memory device for the program, in particular, a connection adapter that is used for an optical tomographic imaging apparatus for ophthalmological care or the like.

2. Description of the Related Art

At present, an optical tomographic imaging apparatus of optical coherence tomography (OCT) utilizing the interference phenomenon of multi-wavelength beams is capable of capturing a tomographic image of a sample with high resolution. Hereinafter, this is referred to as an OCT apparatus.

According to the OCT apparatus described above, a sample is irradiated with measuring beams that is low coherent light, and backscattered light from a sample can be measured by using an interference system.

In addition, the OCT apparatus is capable of capturing a tomographic image with high resolution by scanning the sample with the measuring beams.

Therefore, the OCT apparatus is capable of imaging a tomographic image of a retina of a fundus in a subject eye with high resolution, and hence it is widely used for ophthalmological diagnosis of a retina or the like.

At present, various improvements and refinements of the OCT apparatus have been continuously made, but the apparatus is still expensive and big.

Therefore, the problems of installation space, installing cost, profitability thereof, and the like keep the use of the OCT apparatus only in large hospitals and by some general practitioners.

Conventionally, concerning such OCT apparatus, there is known an OCT apparatus constituting a combination apparatus in which a camera for imaging a two-dimensional image is combined with a tomographic image formation apparatus that is capable of imaging a tomographic image of a fundus and is also capable of imaging a surface image of the fundus by switching with switching means.

Further recently, concerning the OCT apparatus constituting the combination apparatus as described above, there is proposed a fundus observation apparatus as disclosed in Japanese Patent Application Laid-Open No. 2007-181631, in which both a tomographic image and a surface image of a fundus can be captured simultaneously.

This apparatus includes a fundus camera unit and an OCT unit, and the OCT unit can be connected to an optical connector of the fundus camera unit.

As described above, the OCT apparatus is desired to have a small installation space and high profitability for general practitioners to use.

The above-mentioned apparatus disclosed in Japanese Patent Application Laid-Open No. 2007-181631 is capable of capturing both a tomographic image and a surface image of a fundus simultaneously. However, the fundus camera and the OCT apparatus constitute individual units that are connected to each other via the optical connector. Therefore, the apparatus does not always satisfy the requirement for a small installation space.

SUMMARY OF THE INVENTION

The present invention is made in view of the above-mentioned problems, and it is an object of the present invention to provide a connection adapter that is capable of constituting an optical tomographic imaging apparatus having a small installation space, an easily adjustable structure, and high use efficiency, and to provide the optical tomographic imaging apparatus, a program for executing an imaging method and a memory device for the program.

A connection adapter according to the present invention is a connection adapter for connecting a fundus camera main body portion and a camera portion in a detachable manner in an optical tomographic imaging apparatus for imaging a tomographic image of a fundus as an object, being disposed between the fundus camera main body portion and a camera portion to be attached to the fundus camera main body portion for imaging a surface image of the fundus, the connection adapter of the present invention including a first light guide unit for guiding tomographic image measuring beams guided from the fundus camera main body portion for imaging the tomographic image to a tomographic imaging portion, and a second light guide unit for guiding fundus image measuring beams guided from the fundus camera main body portion for imaging the surface image of the fundus to the camera portion.

Further, an optical tomographic imaging apparatus for imaging a tomographic image of a fundus as an object according to the present invention includes a fundus camera main body portion, a camera portion attached to the fundus camera main body portion for imaging a surface image of the fundus, a connection adapter as described above that is disposed between the fundus camera main body portion and the camera portion for connecting the fundus camera main body portion and the camera portion, and a tomographic imaging portion for imaging the tomographic image by the tomographic image measuring beams guided from the first light guide unit in the connection adapter.

Further, a program according to the present invention executes an imaging method of the optical tomographic imaging apparatus for the computer of the above optical tomographic imaging apparatus.

Further, a memory device according to the present invention stores the program and the program is configured so as to be read out by the computer.

The present invention includes a connection adapter that is used for the optical tomographic imaging apparatus and is capable of constituting an optical tomographic imaging apparatus having a small installation space and high use efficiency, the optical tomographic imaging apparatus, a program for executing an imaging method and a memory device for the program can be realized.

Further features of the present invention will become apparent from the following description of exemplary embodiments with reference to the attached drawings.

DESCRIPTION OF THE EMBODIMENTS

Hereinafter, embodiment mode of the present invention is described.

In this embodiment mode, the above-mentioned structure of the present invention is used so as to constitute the connection adapter (400 in FIG. 1A) and the optical tomographic imaging apparatus (200 in FIG. 1A), as described in the following items (1) to (25), for example.

Figure 1A:
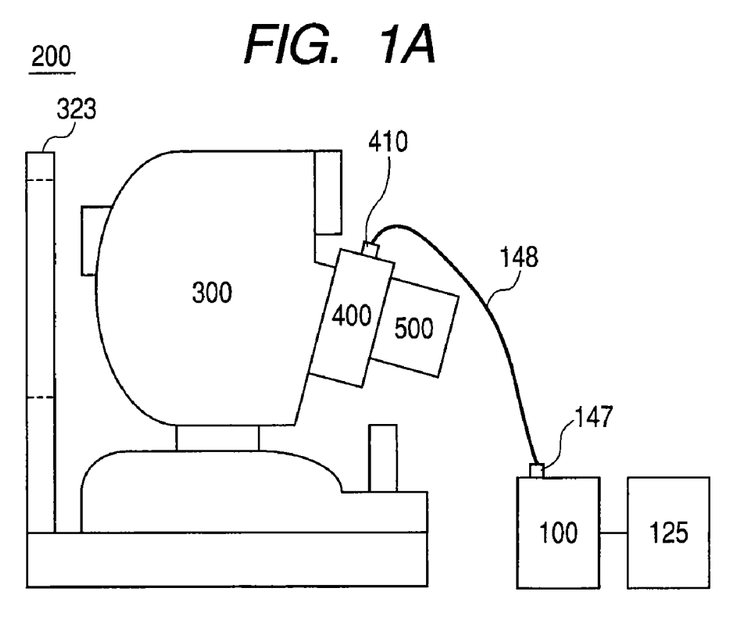
FIGS. 1A and 1B are diagrams illustrating a general structure of an OCT apparatus according to Embodiment 1 of the present invention.

(1) A connection adapter (400) of this embodiment mode includes, as illustrated in FIG. 1A, a connection adapter for connecting a fundus camera main body portion (300) and a camera portion (500) in a detachable manner in the optical tomographic imaging apparatus for imaging a tomographic image of a fundus as an object, being disposed between the fundus camera main body portion (300) and the camera portion (500) to be attached to the fundus camera main body portion for imaging a surface image of the fundus.

Specifically, the connection adapter includes a first light guide unit for guiding tomographic image measuring beams guided from the fundus camera main body portion for imaging the tomographic image to a tomographic imaging portion, and a second light guide unit for guiding fundus image measuring beams guided from the fundus camera main body portion for imaging the surface image of the fundus to the camera portion.

In this case, the fundus camera main body portion guides tomographic image measuring beams for imaging the tomographic image and fundus image measuring beams for imaging the surface image of the fundus with the following structure.

Figure 2A:
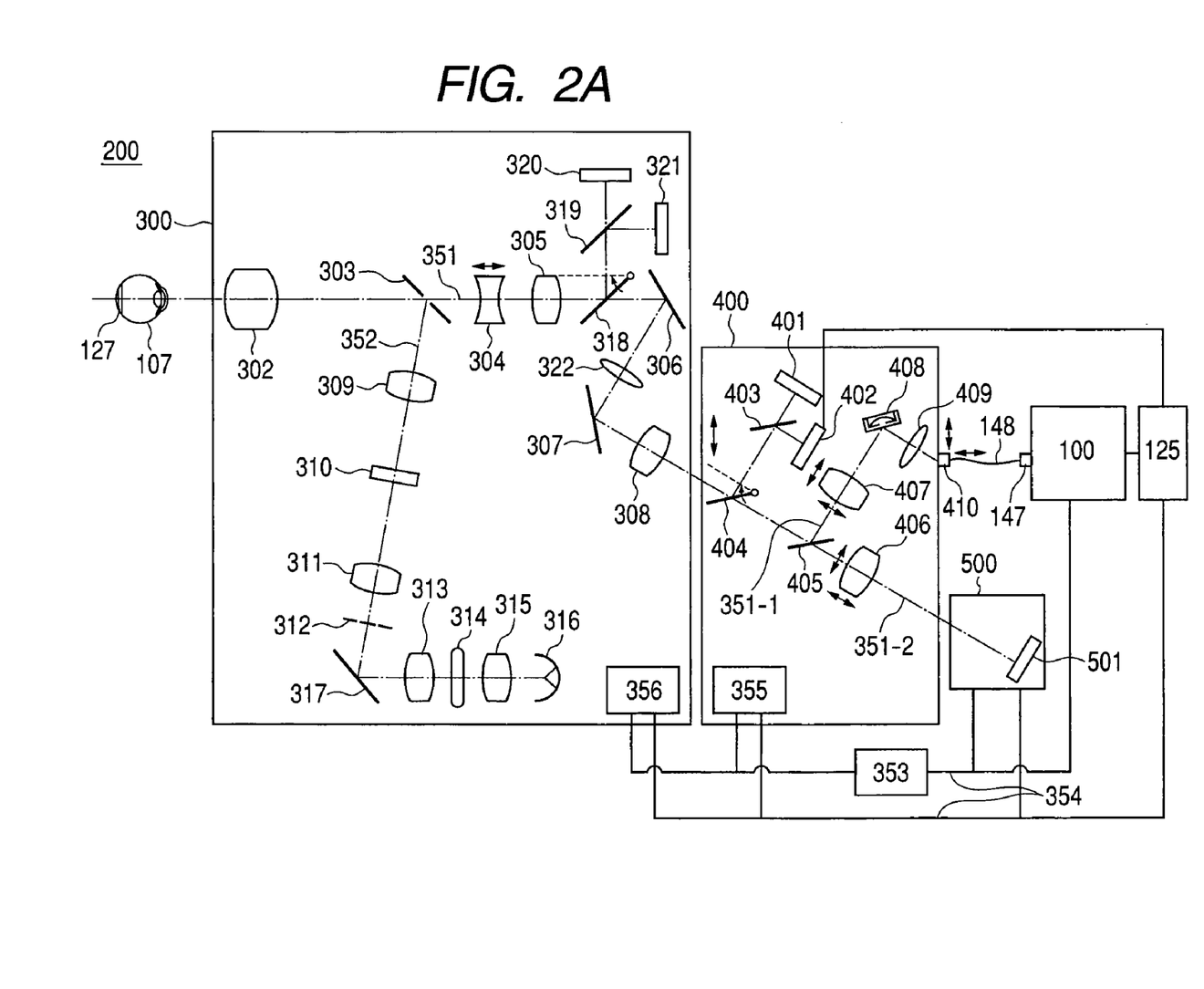
FIG. 2A is a diagram illustrating a structure of an optical system in the OCT apparatus according to Embodiment 1 of the present invention.
Figure 2B:
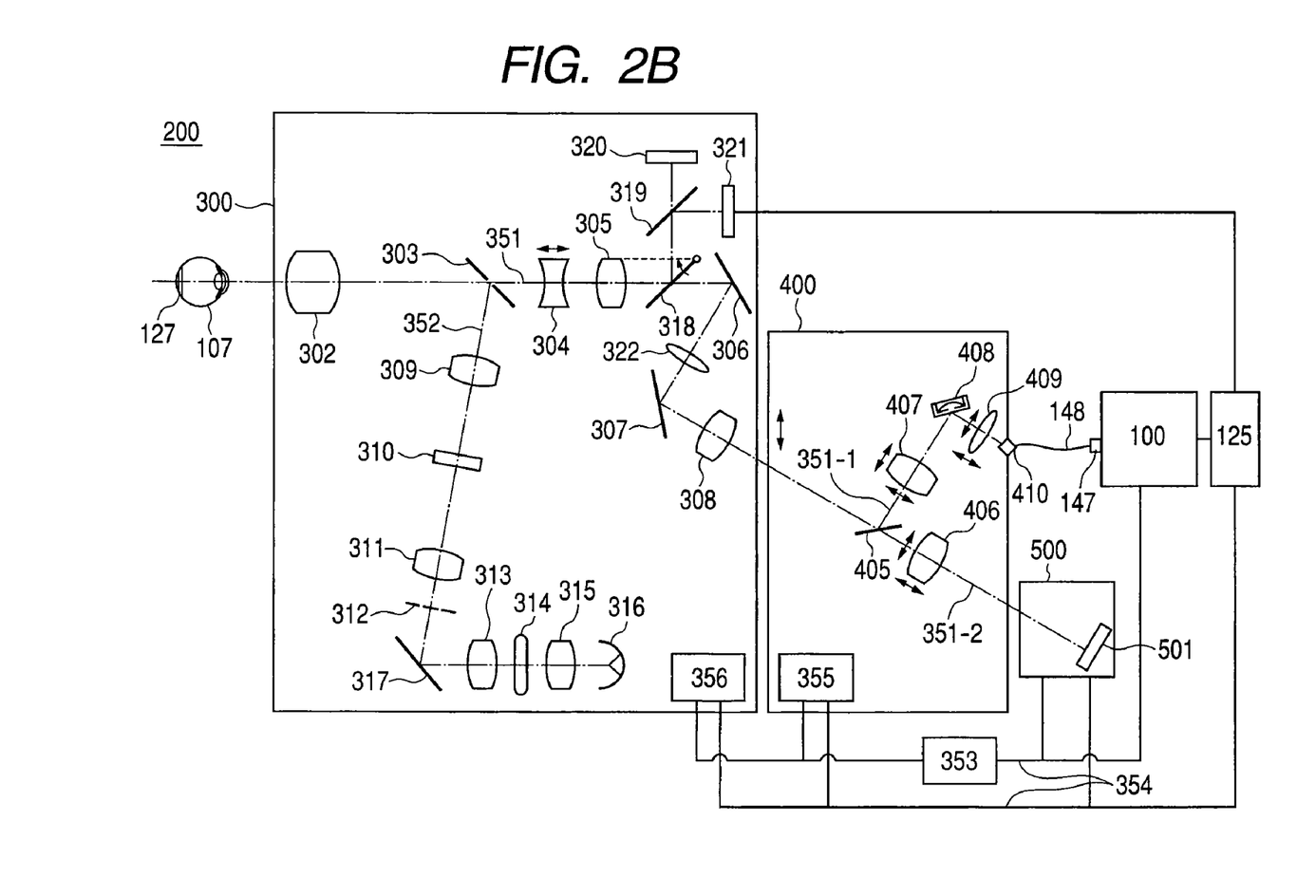
FIG. 2B is a diagram illustrating a structure of an optical system in an OCT apparatus according to Embodiment 2 of the present invention.

For instance, in the fundus camera main body portion 300 illustrated in FIGS. 2A and 2B, a mirror 306, a field lens 322, a mirror 307, and a relay lens 308 in an optical path 351 are capable of constituting the structure for guiding the above-mentioned beams.

In addition, the first light guide unit includes an optical path 351-1 divided by a dichroic mirror 405 illustrated in FIGS. 2A and 2B, a relay lens 407, and the like, for example.

In addition, the second light guide unit includes an optical path 351-2 divided by a dichroic mirror 405 illustrated in FIGS. 2A and 2B, a relay lens 406, and the like, for example.

Using the connection adapter having the above structure, the function of the OCT apparatus can be added to an existing fundus camera. Therefore, it is possible to realize an OCT apparatus having high use efficiency of space and high profitability.

(2) The first light guide unit may have a structure including a scanning optical system (XY scanner 408 in FIGS. 2A and 2B).

Thus, it is easy to guide beams from the first light guide unit to the tomographic imaging portion.

In addition, the structure in which the scanning optical system is disposed inside the connection adapter is adopted, and hence time and effort for adjusting the scanning optical system can be minimized.

(3) The connection adapter of this embodiment mode may have a structure including a beam splitter (dichroic mirror 405 in FIGS. 2A and 2B) for branching at least one of the tomographic image measuring beams and the fundus image measuring beams, so as to guide the beams to the first light guide unit and to the second light guide unit.

Thus, it is possible to branch efficiently the optical path (second light guide unit) for guiding the fundus image measuring beams to the camera portion and the optical path (first light guide unit) for guiding the tomographic image measuring beams to the tomographic imaging portion.

In addition, it is possible to branch the fundus image measuring beams or the tomographic image measuring beams in accordance with a polarization state or a wavelength. Therefore, it is possible to capture the fundus image by visible light and the tomographic image by infrared light, for example.

(4) The connection adapter of this embodiment mode may have a structure including an electric signal relay unit (computer 125 in FIGS. 2A and 2B) for relaying an electric signal between the fundus camera main body portion and the camera portion.

Thus, information can be communicated electrically so that synchronization can be realized easily between the fundus camera main body portion and the camera portion when the fundus image is captured.

(5) The connection adapter of this embodiment mode may have a structure including a fixation lamp (401 in FIG. 2A) for making the eye as an object to gaze at the fixation lamp.

Thus, a fundus image and a tomographic image with little blur can be captured.

(6) The connection adapter of this embodiment mode may have a structure including a quick return mirror (404 in FIG. 2A) in the optical path between the fixation lamp and at least one of the first light guide unit and the second light guide unit.

Thus, the fundus image measuring beams or the tomographic image measuring beams from the subject eye can be guided efficiently to the camera portion or the tomographic imaging portion.

(7) The connection adapter of this embodiment mode may have a structure including an area sensor (402 in FIG. 2A) that is used for registration of the eye as an object, and hence image information captured by the area sensor can be delivered to an image display unit.

Thus, the registration can be performed efficiently so that a fundus image and a tomographic image of a desired part can be easily captured.

(8) It is possible to adopt a structure including the quick return mirror (404 in FIG. 2A) in the optical path between the area sensor and at least one of the first light guide unit and the second light guide unit.

Thus, the fundus image measuring beams or the tomographic image measuring beams from the subject eye can be guided efficiently to the camera portion or the tomographic imaging portion.

(9) The connection adapter of this embodiment mode may have a structure including an electronic circuit (355 and 356 in FIGS. 2A and 2B) for controlling the scanning optical system (408 in FIGS. 2A and 2B), the fixation lamp (401 in FIG. 2A), or the area sensor (402 in FIG. 2A), and the electronic circuit can be driven by electric power supplied from an independent power supply (353 in FIGS. 2A and 2B).

Thus, the quick return mirror, the fixation lamp, the XY scanner, and the like in the connection adapter can be easily controlled.

(10) The connection adapter of this embodiment mode may have a structure including a position adjusting unit for adjusting positions of the fundus camera main body portion and the connection adapter, respectively.

Thus, the positional adjustment of the fundus camera main body portion and the connection adapter can be performed, and the connection adapter can be attached to various types of the fundus camera main body portions.

(11) The connection adapter of this embodiment mode may have a structure including an optical axis adjusting unit for adjusting a positional relationship of the individual optical axes of the fundus camera main body portion and the connection adapter.

Thus, the adjustment can be performed so that the optical axis of the fundus camera main body portion and the optical axis of the connection adapter are positioned on the same axis.

In addition, the connection adapter can be attached to various types of the fundus camera main body portions.

(12) The connection adapter of this embodiment mode may include an adjusting unit (409 in FIGS. 2A and 2B) for adjusting a focal position of the tomographic image measuring beams. Thus, the focal position can be adjusted so that the tomographic image measuring beams is condensed onto a desired position of the object. In addition, the focal position can be adjusted independently of a focal position of the fundus camera.

(13) The connection adapter of this embodiment mode may have a structure in which the beam splitter guides some wavelengths of the tomographic image measuring beams to the second light guide unit. Thus, a part of the tomographic image measuring beams is guided to the camera portion side, and hence the tomographic image measuring beams can be observed from the camera portion side during the optical axis adjustment.

(14) The optical tomographic imaging apparatus of this embodiment mode may have a structure including a fundus camera main body portion (300 in FIG. 1A) in the optical tomographic imaging apparatus for imaging a tomographic image of the fundus as an object, a camera portion (500 in FIG. 1A) for imaging the surface image of the fundus that is attached to the fundus camera main body portion, a connection adapter (400 in FIG. 1A) having any one of the structures described above that is disposed between the fundus camera main body portion and the camera portion for connecting the fundus camera main body portion and the camera portion to each other, and a tomographic imaging portion (100 in FIG. 1A) for imaging the tomographic image with the tomographic image measuring beams guided from a third light guide unit in the connection adapter.

With this structure, the function of the OCT apparatus can be added to an existing fundus camera, and hence it is possible to realize an OCT apparatus having high use efficiency of space and high profitability.

The optical tomographic imaging apparatus can be configured in a manner that a program to execute the imaging method to a computer of the optical tomographic imaging apparatus is stored in a memory device so that the computer can read out the program.

(15) The optical tomographic imaging apparatus of this embodiment mode may have a structure in which at least two of the fundus camera main body portion, the tomographic imaging portion, the camera portion, and the connection adapter may be supplied with electric power from a common power supply (353 in FIGS. 2A and 2B).

With this structure, wirings for supplying power from the outside can be simplified.

(16) The optical tomographic imaging apparatus of this embodiment mode may have a structure in which, when the fundus camera main body portion is attached to the connection adapter, the quick return mirror (318 in FIGS. 2A and 2B, and 404 in FIG. 2A) of the fundus camera main body portion can be controlled.

With this structure, when imaging, one of the quick return mirrors disposed in the fundus camera main body portion and the connection adapter can be selected for use.

(17) The optical tomographic imaging apparatus of this embodiment mode may have a structure including an image display unit (computer 125 in FIGS. 2A, 2B, and 3) for displaying a positional relationship between the fundus image captured by the camera portion and the tomographic image captured by the tomographic imaging portion with association.

When the positional relationship between the fundus image captured by the camera portion and the tomographic image captured by the tomographic imaging portion is displayed with association in this way, a state of the subject eye can be grasped easily. Further, it is possible to capture a three-dimensional image.

Figure 3:
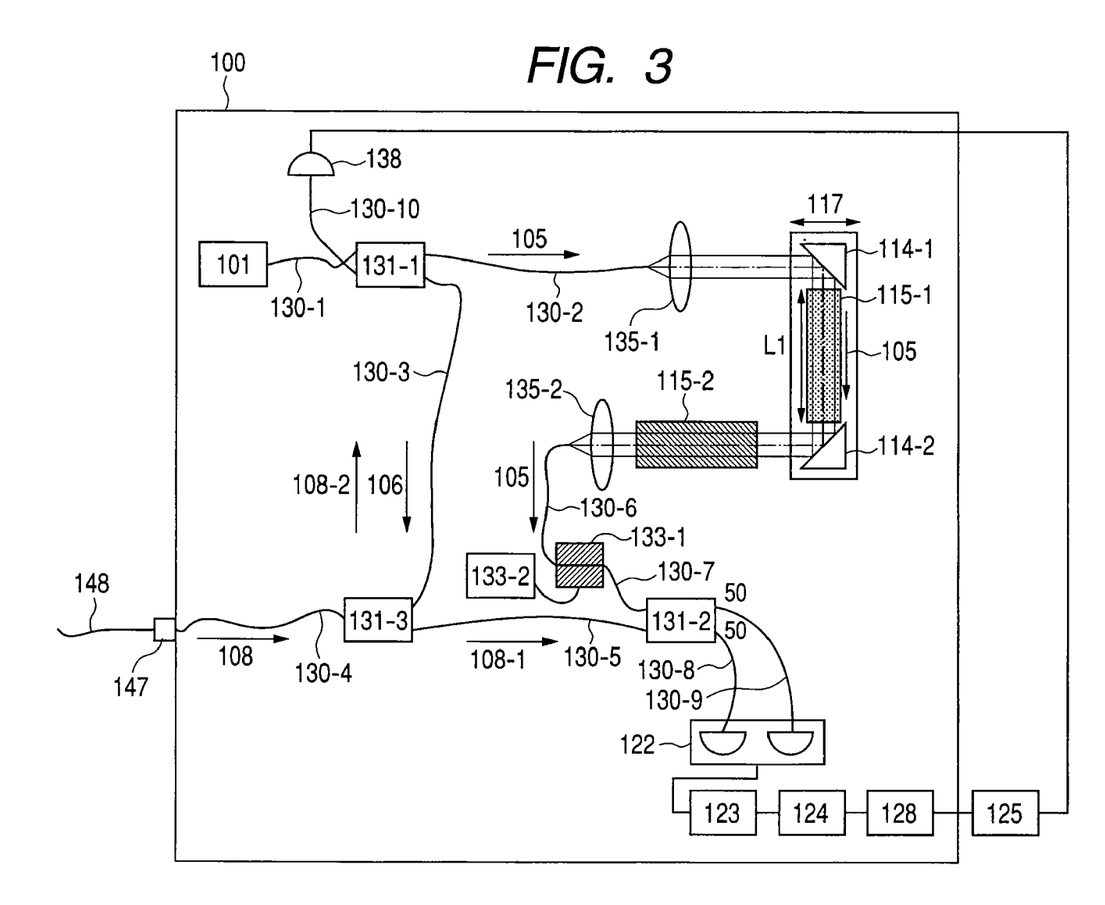
FIG. 3 is a diagram illustrating a structure of an OCT imaging portion in the optical system according to Embodiment 1 of the present invention.

(18) The optical tomographic imaging apparatus of this embodiment mode may have a structure in which the tomographic imaging portion includes a dispersion compensation unit (dispersion compensating glasses 115-1 and 115-2 in FIG. 3).

With this structure, it is possible to compensate for an optical dispersion difference between the fundus camera main body portion and the tomographic imaging portion.

In addition, it is also possible to compensate for dispersion with respect to any fundus camera main body portion.

(19) The optical tomographic imaging apparatus of this embodiment mode may have a structure including a position adjusting unit for adjusting positions of the fundus camera main body portion and the connection adapter, respectively.

Thus, the positional adjustment of the fundus camera main body portion and the connection adapter can be performed, and the connection adapter can be attached to various types of the fundus camera main body portions.

(20) The optical tomographic imaging apparatus of this embodiment mode may have a structure including an optical axis adjusting unit for adjusting a positional relationship of the individual optical axes of the fundus camera main body portion and the connection adapter.

Thus, the adjustment can be performed so that the optical axis of the fundus camera main body portion and the optical axis of the connection adapter are positioned on the same axis.

In addition, the connection adapter can be attached to various types of the fundus camera main body portions.

(21) The optical tomographic imaging apparatus of this embodiment mode may have a structure in which at least some of the fundus camera main body portion, the connection adapter, the camera portion, and the tomographic imaging portion are controlled by a common control unit, and hence synchronization between the above-mentioned components can be maintained easily. For instance, the adjustment of the focal position can be easily synchronized with imaging timing.

(22) The optical tomographic imaging apparatus of this embodiment mode may have a structure in which the beam splitter guides some of wavelengths of the tomographic image measuring beams to the second light guide unit. Thus, a position of the tomographic image measuring beams can be observed from the camera portion side of the adapter, so as to be utilized for reference of the optical axis adjustment of the tomographic image measuring beams.

(23) The optical tomographic imaging apparatus of this embodiment mode may have a fundus conjugate plane (601 in FIG. 5A) that is substantially conjugate optically with the fundus position in the fundus camera main body portion. Thus, even if the fundus camera main body portion has a long optical path, the adjustment can be easily performed by referring the fundus conjugate plane.

(24) The optical tomographic imaging apparatus of this embodiment mode may include a chart (801 in FIG. 5A) for indicating the optical axis of the fundus camera main body portion so as to be inserted in the fundus conjugate plane. Thus, the optical axis adjustment of the tomographic image measuring beams becomes more precise and simple.

(25) The optical tomographic imaging apparatus of this embodiment mode may have a structure in which the camera portion is sensitive to at least some of wavelengths of the tomographic image measuring beams. Thus, observation of the tomographic image measuring beams during the optical axis adjustment can be performed by using the camera portion, and hence a special tool or a jig for the observation is not necessary.

EMBODIMENTS

Next, embodiments of the present invention are described.

Embodiment 1

In Embodiment 1, a connection adapter and an OCT apparatus to which the present invention is applied are described.

Here, in particular, an apparatus for imaging a tomographic image (OCT image) and a fundus image (plane image) of a subject eye is described.

In this embodiment, a time domain OCT (TD-OCT) is described particularly concerning imaging a tomogram. However, the present invention can be applied not only to such TD-OCT but also to a fourier domain OCT (FD-OCT).

First, a general structure of the OCT apparatus including the connection adapter according to this embodiment is described with reference to FIGS. 1A and 1B.

Figure 1B:
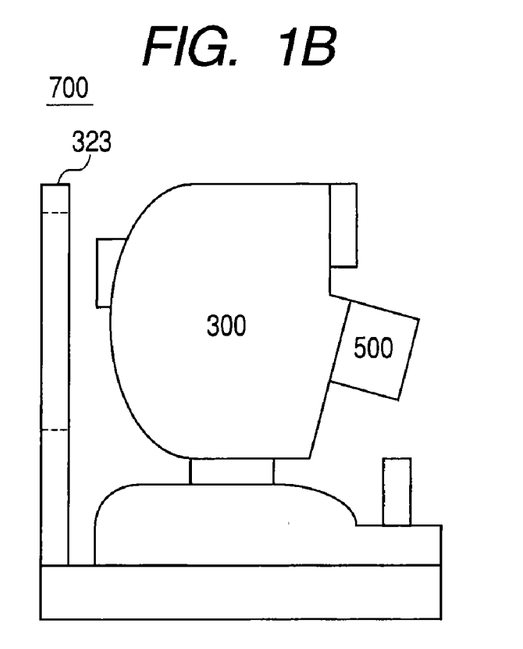

FIGS. 1A and 1B are diagrams illustrating the general structure of this embodiment.

FIG. 1A is a side view illustrating a structure in which a camera is connected optically to the fundus camera main body portion of the OCT apparatus via the connection adapter.

In addition, FIG. 1B is a diagram illustrating a structure in which the camera is attached to the fundus camera main body portion of the OCT apparatus without using a connection adapter.

In FIGS. 1A and 1B, the OCT apparatus 200 includes an OCT imaging portion 100, the fundus camera main body portion 300, the connection adapter 400, and a camera portion 500 of the existing camera.

In this embodiment, as illustrated in FIG. 1A, the camera portion 500 is attached to the fundus camera main body portion of the OCT apparatus via the connection adapter 400 so that they are optically connected to each other.

In addition, the fundus camera main body portion 300 and the connection adapter 400 are supported in a relatively movable manner so that positional adjustment can be performed, which is a feature of the present embodiment.

In addition, the connection adapter 400 and the OCT imaging portion 100 are structured to be optically connected with each other via an optical fiber 148.

In this case, the connection adapter 400 is provided with a connector 410, and the OCT imaging portion 100 is provided with a connector 147, which enable the OCT imaging portion 100 to be attached and detached easily to the connection adapter 400. In addition, the connector 410 is supported in a movable manner in a direction perpendicular or horizontal to the optical axis so that the optical axis adjustment can be performed, which is one of features of the present embodiment.

In addition, a chin support 323 fixes a chin and a forehead of a subject so that the subject eye is fixed for imaging the image.

A computer 125 creates and displays a tomographic image.

In addition, as illustrated in FIG. 1B, the camera portion 500 may be attached to the fundus camera main body portion 300 without using the connection adapter 400, and therefore one fundus camera 700 can be constituted.

In the fundus camera 700 having such structure, the camera portion 500 is removed from the fundus camera main body portion 300, and the connection adapter 400 is attached between the camera portion 500 and the fundus camera main body portion 300.

Thus, the OCT apparatus 200 provided with the camera portion 500 can be constituted.

Here, the camera portion 500 can be a general-purpose digital single-lens reflex camera or the like that is existing and used generally.

The camera portion 500 and the connection adapter 400 or the fundus camera main body portion 300 are structured to be mounted by using a general-purpose camera mount.

Next, a concrete structure of the optical system of the OCT apparatus including the connection adapter according to this embodiment is described.

FIG. 2A is a diagram illustrating a concrete structure of the optical system according to this embodiment.

In FIG. 2A, the same structure as in FIGS. 1A and 1B is denoted by the same reference numeral, and hence overlapping description is omitted.

In FIG. 2A, a subject eye is represented by 107, and a retina is represented by 127.

The OCT apparatus 200 of this embodiment is constituted so as to use the OCT imaging portion 100 and the camera portion 500 for capturing the tomographic image (OCT image) and the fundus image (plane image) of the retina 127 of the subject eye 107.

First, the fundus camera main body portion 300 is described.

In FIG. 2A, the fundus camera main body portion 300 includes an objective lens 302, a perforated mirror 303, a focus lens 304, an imaging lens 305, a relay lens 308, an optical filter 310, a ring slit 312, and condenser lenses 313 and 315.

Also, the fundus camera main body portion 300 includes a stroboscopic tube 314, a halogen lamp 316, a quick return mirror 318, a dichroic mirror 319, a fixation lamp 320, an area sensor 321, and a field lens 322.

Further, the fundus camera main body portion 300 includes optical paths 351 and 352, a power supply 353, a cable 354, and electronic circuits 355 and 356.

In the fundus camera main body portion 300 of this embodiment, the objective lens 302 is disposed so as to be opposed to the subject eye 107, and the optical path is divided into the optical path 351 and the optical path 352 by the perforated mirror 303 on the optical axis.

The optical path 352 forms an illumination optical system for illuminating the fundus of the subject eye 107.

In the lower part of the fundus camera main body portion 300, there are disposed the halogen lamp 316 that is used for registration of the subject eye 107 and the stroboscopic tube 314 that is used for imaging the image of the fundus of the subject eye 107.

Here, the fundus camera main body portion 300 includes a mirror 317. Illuminating light from the halogen lamp 316 and the stroboscopic tube 314 becomes a ring-like light beam by the ring slit 312 and is reflected by the perforated mirror 303 so as to illuminate the fundus of the subject eye 107.

Here, the fundus camera main body portion 300 includes lenses 309 and 311.

The optical path 351 forms an optical system for imaging the tomographic image and the fundus image of the fundus of the subject eye 107.

The focus lens 304 and the imaging lens 305 are disposed on the right part in the diagram of the perforated mirror 303.

Here, the focus lens 304 is supported in a movable manner in the optical axis direction indicated by the arrow in FIG. 2A.

Next, the optical path 351 is led via the quick return mirror 318 to the fixation lamp 320 and the area sensor 321.

Here, the quick return mirror 318 includes a silver film and a protection film thereof formed in this order on the surface thereof.

In addition, a dichroic mirror 319 is designed so that visible light is guided toward the fixation lamp 320 while infrared light is guided toward the area sensor 321.

In addition, the optical path 351 is led to the connection adapter 400 via the mirror 306, the field lens 322, the mirror 307, and the relay lens 308.

In addition, the power supply 353 supplies electric power via the cable 354 to the OCT imaging portion 100, the fundus camera main body portion 300, the connection adapter 400, and the camera portion 500.

As the power supply is integrated as one unit in this way, connection between devices can be performed easily.

In addition, an electronic circuit 356 is disposed for a purpose of controlling the quick return mirror 318 and the focus lens 304. Electric power for the controlling of these elements is supplied from the power supply 353.

In addition, with its structure, when the fundus imaging, an electric signal can be relayed by the computer 125 and the electronic circuit 356 between the fundus camera main body portion 300 and the camera portion 500 so that electric information can be communicated between them for synchronization or the like.

Next, the connection adapter 400 is described.

In FIG. 2A, the connection adapter 400 includes a fixation lamp 401, an area sensor 402, a dichroic mirror 403, a quick return mirror 404, and a dichroic mirror 405.

Also, the connection adapter 400 includes relay lenses 406 and 407, an XY scanner 408, a collimate lens 409, and a connector 410.

The connection adapter 400 of this embodiment has a main function of dividing the optical path 351 into the optical path 351-1 for imaging the tomographic image and the optical path 351-2 for imaging the fundus image by using the dichroic mirror 405.

Note that the optical path 351-1 for imaging the tomographic image corresponds to the first light guide unit while the optical path 351-2 for imaging the fundus image corresponds to the second light guide unit.

Here, the relay lenses 406 and 407 are retained in a movable manner, so that each of the optical axes of the optical paths 351-1 and 351-2 can be adjusted by performing fine positional adjustment. In addition, for simplicity of description here, the XY scanner 408 constituting the scanning optical system is described as one mirror.

However, two mirrors for X scanning and Y scanning are actually disposed closely to each other, so that the retina 127 is raster-scanned in the direction perpendicular to the optical axis.

In addition, the optical axis of the optical path 351-1 is adjusted so as to agree with the rotation center of the two mirrors of the XY scanner 408.

In addition, the connector 410 is a connector for attaching the optical fiber 148.

Further, the connection adapter 400 includes a fixation lamp 401 and an area sensor 402, which are similar to corresponding elements in the fundus camera main body portion 300.

The collimate lens 409 has a role of converting the beams propagating in the optical fiber 148 into a parallel beam. Further, the collimate lens 409 is supported in a movable manner and can also be used for adjusting the focus of the retina 127 as an object. In addition, the computer 125 is capable of performing the positional adjustment of the collimate lens via the electronic circuit 355.

The image information captured by the area sensor 402 is displayed by using the computer 125 and is used for registration of the subject eye.

The dichroic mirror 403 is also designed to be similar to the dichroic mirror in the fundus camera main body portion 300 so that visible light is guided toward the fixation lamp 401 while infrared light is guided toward the area sensor 402.

Here, the quick return mirror 404 is designed to reflect a part of the infrared light and to reflect visible light.

As the quick return mirror 404 is designed to reflect a part of the infrared light, the fixation lamp 401, the area sensor 402, and the OCT imaging portion 100 can be used simultaneously.

In addition, an electronic circuit 355 is disposed for a purpose of controlling the fixation lamp 401, the area sensor 402, and the XY scanner 408.

The connection adapter 400 and the camera portion 500 are attached by a general-purpose camera mount.

Therefore, the connection adapter 400 can be attached or detached easily. The fundus image is formed on the surface of an area sensor 501.

Next, a structure of the OCT imaging portion 100 is described.

FIG. 3 is a diagram illustrating a structure of the OCT imaging portion 100.

In FIG. 3, the OCT imaging portion includes light source 101, reference beams 105, the measuring beams 106, return beams 108, mirrors 114-1 and 114-2, dispersion compensating glasses 115-1 and 115-2, and an electric stage 117.

Also, the OCT imaging portion includes a balanced detector 122, an amplifier 123, a filter 124, a computer 125, and an AD converter 128.

Further, the OCT imaging portion includes single mode fibers 130-1 to 130-10, optical couplers 131-1 to 131-3, and an acoustooptical modulator element 133-1 and a controller 133-2 for the element 133-1.

In this embodiment, the OCT imaging portion 100 is used for capturing the tomogram of the retina 127 of the subject eye 107.

In addition, using the optical fiber for constituting a part of the optical system, a downsizing is realized. The optical fiber is used as the optical path in this embodiment, but it is not always necessary to use the optical fiber.

Next, the structure of the optical system in the OCT imaging portion 100 is described.

The OCT imaging portion 100 constitutes a Mach-Zehnder interference system as a whole as illustrated in FIG. 3.

In FIG. 3, the light emitted from the light source 101 is divided into the reference beams 105 and the measuring beams 106 by the optical coupler 131-1.

The measuring beams 106 are led to the connector 147 via the optical coupler 131-3.

After that, via the connection adapter 400 and the fundus camera main body portion 300, the measuring beams 106 are reflected or scattered by the subject eye 107 to be observed so as to become return beams 108-1, which arecombined with the reference beams 105 by the optical coupler 131-2.

The reference beams 105 and the return beams 108-1 are combined and afterward divided so as to enter the balanced detector 122. Using light intensity captured by the balanced detector 122, the tomogram of the subject eye 107 is constituted.

Next, peripheries of the light source 101 are described.

The light source 101 is a super luminescent diode (SLD) that is a typical low coherent light source, having a wavelength of 830 nm and a band width of 50 nm.

Here, the band width is an important parameter because it affects a resolution of the captured tomogram in the optical axis direction.

In addition, the SLD is selected as a type of the light source here, but amplified spontaneous emission (ASE) type or the like that can emit low coherent light may also be used.

In addition, concerning the wavelength, near infrared light is suitable in view of measuring an eye. Further, as the wavelength affects the resolution of the captured tomogram in the lateral direction, the wavelength is preferably as short as possible, and here, 830 nm is selected. Depending on a part of the subject to be measured, another wavelength may be selected.

The light emitted from the light source 101 is led to the optical coupler 131-1 through the single mode fiber 130-1 and is divided at an intensity ratio of 10:90, so as to be the measuring beams 106 and the reference beams 105, respectively.

Next, the optical path of the reference beams 105 is described.

The reference beams 105 divided by the optical coupler 131-1 are led to the lens 135-1 through the single mode fiber 130-2 and are adjusted to be a parallel beam having a diameter of 4 mm.

Next, the reference beams 105 enter reference mirrors 114-1 and 114-2 successively and are led to the single mode fiber 130-6 by the lens 135-2.

Here, the dispersion compensating glasses 115-1 and 115-2 through which the reference beams 105 pass are dispersion compensating glasses.

The dispersion compensating glass 115-1 has a length Ll, which is preferably two times the depth of a typical eye.

The dispersion compensating glass 115-1 compensates for dispersion of the measuring beams 106 propagating to and back from the subject eye 107 with respect to the reference beams 105.

Here, it is supposed that Ll is 46 mm that is two times 23 mm as a diameter of an average Japanese eyeball.

In addition, the dispersion compensating glass 115-2 compensates for dispersion of the measuring beams 106 and the returning beams 108 propagating along the optical path 351 between the fundus camera main body portion 300 and the connection adapter 400 with respect to the reference beams 105.

In addition, the electric stage 117 is capable of moving in the direction indicated by the arrow in the diagram so that the optical path length of the reference beams 105 can be adjusted and controlled.

Further, the reference beams 105 pass through the acoustooptical modulator element 133-1 and the single mode fiber 130-7, so as to enter the optical coupler 131-2.

Here, the acoustooptical modulator element 133-1 is for the optical fiber and is capable of performing frequency shift of 1 MHz by using the controller 133-2.

Next, the optical path of the measuring beams 106 is described.

The measuring beams 106 divided by the optical coupler 131-1 propagate in the single mode fiber 130-3 and enter the optical coupler 131-3.

After that, the measuring beams 106 are led to the connector 147 through the single mode fiber 130-4.

After that, the measuring beams 106 are led to the retina of the subject eye 107 through the optical fiber 148, the optical connector 410, the connection adapter 400, and the fundus camera main body portion 300.

When the measuring beams 106 enters the subject eye 107, they are reflected or scattered by the retina 127 so as to be the return beams 108.

Further, the return beams 108 are divided into the return beams (first return beams) 108-1 and the return beams (second return beams) 108-2 by the optical coupler 131-3. One of them, i.e., the return beams 108-2 pass through the optical coupler 131-1 and are led to a detector 138.

Here, the detector 138 is, for example, an avalanche photo diode (APD) that is an optical sensor with high speed and high sensitivity.

In addition, the other return beams 108-1 pass through the single mode fiber 130-5 and the optical coupler 131-2, and are led to the balanced detector 122.

Next, the structure of a measuring system of the OCT imaging portion 100 according to this embodiment is described.

The OCT imaging portion 100 is capable of capturing the tomographic image (OCT image) constituted of an interference-signal intensity by a Mach-Zehnder interference system.

Its measuring system is described. The return beams 108-1, that is, one of the divided return beams 108 reflected and scattered by the retina 127 is combined with the reference beams 105 by the optical coupler 131-2 and are further divided at a 50:50 ratio.

Next, each of the divided beams is led to the balanced detector 122 through the single mode fiber 130-8 or 130-9, thereby converting the intensity of the combination beams of the reference beams 105 and the return beams 108-1 into a voltage.

The obtained voltage signal is amplified by the amplifier 123, and the filter 124 extracts a necessary frequency component. The AD converter 128 converts the voltage signal into a digital value, and the computer 125 performs demodulation and data processing so as to form the tomogram.

In addition, the other return beams 108-2 of the above-mentioned divided return beams 108 pass through the optical coupler 131-1 and the optical fiber 130-10, and are led to the detector 138.

Further, the detector 138 is electrically connected to the computer 125, so that the intensity of the return beams 108-2 can be recorded and displayed.

In addition, the signal obtained in the detector 138 is the intensity signal of the return beams 108-2 reflected or scattered by the retina 127 and has no depth resolution unlike the above-mentioned interference signal.

Next, a method of capturing the tomogram by using the OCT apparatus 200 is described.

The OCT apparatus 200 is capable of controlling the electric stage 117 (FIG. 3) and the XY scanner 408 so as to capture the tomogram of a desired part of the retina 127 (see FIG. 2A).

When imaging, the quick return mirror 318 in the fundus camera main body portion 300 is flipped up (broken line) so that the fixation lamp 320 or the area sensor 321 is not used.

In contrast, the quick return mirror 404 in the connection adapter 400 is not flipped up (solid line).

In addition, it is also possible to image the image with the quick return mirror 404 flipped up for a purpose of improving imaging sensibility. The positional adjustment of the subject eye 107 before imaging the image is performed in the state where the halogen lamp 316 illuminates the retina 127 and the image information captured by the area sensor 402 is displayed by using the computer 125.

Appropriately, the fixation lamp 401 is used for urging the subject eye to be fixed for adjusting the position or the like of the subject eye 107 so that a desired part of the retina 127 can be observed.

Next, a method of capturing the tomogram (of the surface parallel to the optical axis) of the retina 127 is described with reference to FIGS. 4A and 4B.

Figure 4A:
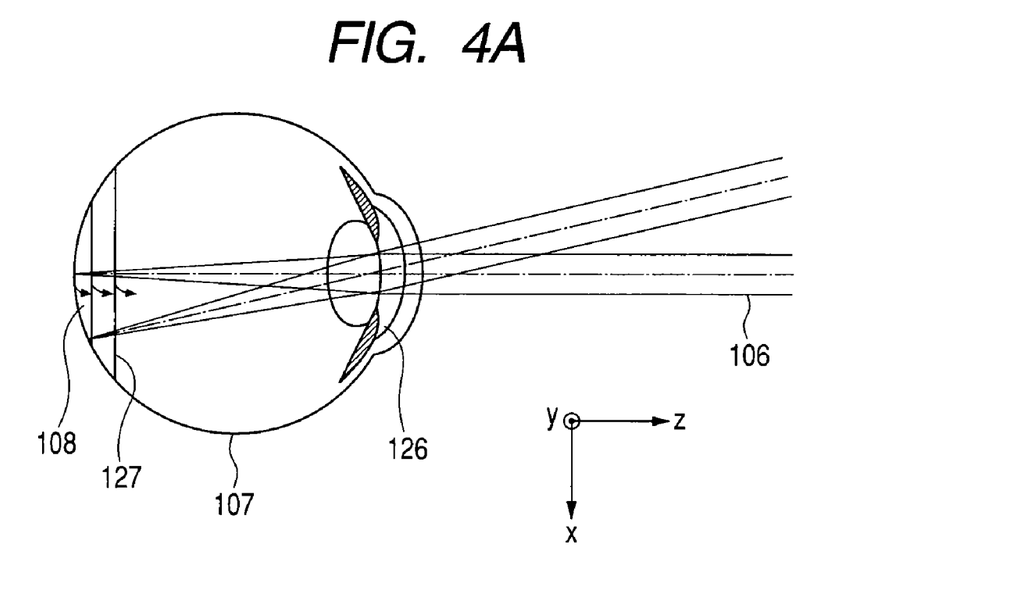
FIGS. 4A and 4B are diagrams illustrating an imaging method of a tomographic image according to Embodiment 1 of the present invention.
Figure 4B:
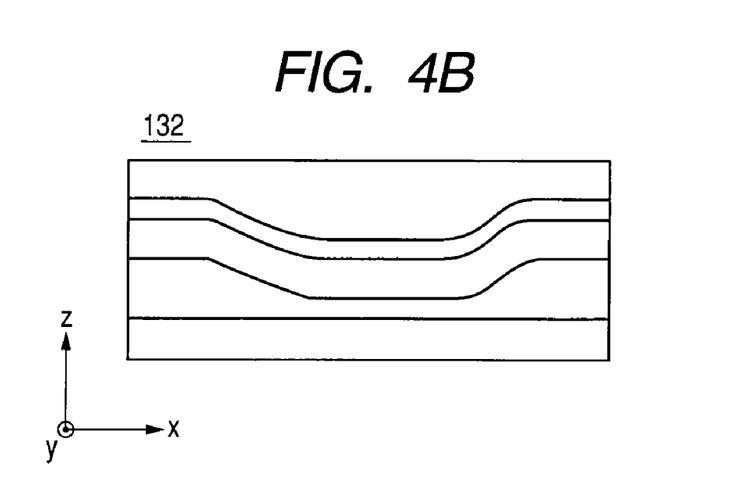

FIG. 4A is a schematic diagram of the subject eye 107 and illustrates the state observed by the OCT apparatus 200.

As illustrated in FIG. 4A, the measuring beams 106 enters the retina 127 through the cornea 126 so as to be the return beams 108 reflected or scattered at various positions and to reach the balanced detector 122 with time delay corresponding to each of the positions.

In this case, the light source 101 has a wide band width and a short coherence length. Therefore, the interference signal can be detected by the balanced detector 122 only if an optical path length of a reference optical path is equal to an optical path length of a measuring beams path.

As described above, the frequency of the reference beams 105 is 1 MHz shift from the measuring beams 106, and hence the interference signal becomes a beat signal of 1 MHz.

Further, if the interference signal is detected while driving the X axis of the XY scanner 408, the interference signal becomes a signal having positional information in the X axis.

The amplitude of this signal is squared and is demodulated so that intensity distribution of the return beams 108 in the X axis direction on an arbitrary XY plane can be captured.

Further, the same operation is repeated while moving the optical path length of the reference optical path by using the electric stage 117. Then, two-dimensional distribution of intensity of the return beams 108 on the XZ plane is obtained, which is the tomogram 132 (FIG. 4B).

The tomogram 132 is inherently distribution in which intensities of the interference signal are arranged like an array as described above. For instance, in this distribution, intensities of the interference signal are applied to gray scales and displayed. Here, only the boundary of the captured tomogram is emphasized and displayed.

Next, a method of capturing the fundus image by using the OCT apparatus 200 is described.

The OCT apparatus 200 is capable of capturing the fundus image of the retina 127 (see FIG. 2A) by using the camera portion 500.

In adjustment before imaging, the quick return mirror 318, similarly to the above-mentioned tomogram, is flipped up (broken line) so that the fixation lamp 320 or the area sensor 321 is not used.

The positional adjustment of the subject eye 107 before imaging the image is performed in the state where the halogen lamp 316 illuminates the retina 127 and the retina 127 is observed by the area sensor 402.

Appropriately, the fixation lamp 401 is used for urging the subject eye to be fixed for adjusting the position or the like of the subject eye 107 so that a desired part of the retina 127 can be observed.

When the adjustment is finished, the stroboscopic tube 314 is activated to emit light. At the same time, the quick return mirror 404 is flipped up, so that the fundus image is captured by using the camera portion 500 and is displayed.

Appropriately, positions of the fundus image and the tomogram 132 are associated with each other and are displayed by using the computer 125.

Embodiment 2

In Embodiment 2, a connection adapter and an OCT apparatus to which the present invention is applied are described.

Embodiment 2 has a structure in which the connection adapter has no fixation lamp and no area sensor.

Optical systems of a fundus camera and the connection adapter are the same as in Embodiment 1 except for some items. Therefore, structures of only an optical system of a fundus camera main body portion and an optical system of the connection adapter are described below.

A structure of an optical system of an OCT apparatus including the connection adapter according to this embodiment is described.

FIG. 2B is a diagram illustrating the structure of the optical system according to this embodiment.

In FIG. 2B, the same structure as in FIGS. 1A, 1B and 2A is denoted by the same reference numeral.

The OCT apparatus 200 of this embodiment is constituted so as to use an OCT imaging portion 100 and a camera portion 500 for capturing a tomographic image (OCT image) and a fundus image (plane image) of a retina 127 of a subject eye 107.

First, the fundus camera main body portion 300 is described.

Objective lens 302 is disposed so as to be opposed to the subject eye 107, and an optical path is divided into an optical path 351 and an optical path 352 by a perforated mirror 303 on its optical axis.

The optical path 352 forms an illumination optical system for illuminating the fundus of the subject eye 107. In the lower part of the fundus camera main body portion 300, there are disposed a halogen lamp 316 that is used for registration of the subject eye 107 and a stroboscopic tube 314 that is used for imaging the image of the fundus of the subject eye 107.

The fundus camera main body portion 300 includes condenser lenses 313 and 315, and a mirror 317.

Illuminating light from the halogen lamp 316 and the stroboscopic tube 314 becomes a ring-like light beam by a ring slit 312 and is reflected by the perforated mirror 303 so as to illuminate the fundus of the subject eye 107.

In addition, the fundus camera main body portion 300 includes lenses 309 and 311, and an optical filter 310.

The optical path 351 forms an optical system for imaging the tomographic image and the fundus image of the fundus of the subject eye 107.

A focus lens 304 and an imaging lens 305 are disposed on the right of the perforated mirror 303.

Here, the focus lens 304 is supported in a movable manner in the optical axis direction indicated by the arrow in FIG. 2B.

Next, the optical path 351 is led via a quick return mirror 318 to a fixation lamp 320 and an area sensor 321.

Here, the quick return mirror 318 is designed to reflect a part of infrared light and to reflect visible light.

As the quick return mirror 318 is designed to reflect a part of the infrared light, the fixation lamp 320, the area sensor 321, and the OCT imaging portion 100 can be used simultaneously.

In addition, a dichroic mirror represented by 319 is designed so that the visible light is guided toward the fixation lamp 320 while the infrared light is guided toward the area sensor 321.

The image information captured by the area sensor 321 is displayed by using a computer 125 and is used for registration of the subject eye.

Next, the optical path 351 is led to the connection adapter 400 via a mirror 306, a field lens 322, a mirror 307, and a relay lens 308.

Next, the configuration of the connection adapter 400 of this embodiment is described with reference to FIG. 2B.

The connection adapter 400 has a main function of dividing the optical path 351 into an optical path 351-1 for imaging the tomographic image and an optical path 351-2 for imaging the fundus image by using a dichroic mirror 405.

Here, the connection adapter 400 includes relay lenses 406 and 407, an XY scanner 408, and a collimate lens 409.

Here, the relay lenses 406 and 407 are retained in a movable manner, so that the optical axes of the optical paths 351-1 and 351-2 can be adjusted by performing fine positional adjustment. Here, for simple description, the XY scanner 408 is described as one mirror. However, actually the XY scanner 408 includes two mirrors for X scanning and Y scanning, disposed closely to each other, so that the retina 127 is raster-scanned in the direction perpendicular to the optical axis. In addition, the optical axis of the optical path 351-1 is adjusted so as to agree with the rotation center of the two mirrors of the XY scanner 408. In addition, a connector represented by 410 is used for attaching the optical fiber 148.

Next, a method of capturing the tomogram by using the OCT apparatus 200 of this embodiment is described.

The OCT apparatus 200 is capable of controlling the electric stage 117 (FIG. 3) and the XY scanner 408 so as to capture the tomogram of a desired part of the retina 127 (see FIG. 2B).

When imaging, the quick return mirror 318 is set not to be flipped up (solid line). The positional adjustment of the subject eye 107 before imaging the image is performed in the state where the halogen lamp 316 illuminates the retina 127 and the retina 127 is observed by the area sensor 321.

Appropriately, the fixation lamp 320 is used for urging the subject eye to be fixed for adjusting the position or the like of the subject eye 107 so that a desired part of the retina 127 can be observed.

A method of capturing the tomogram of the retina 127 is the same as in Embodiment 1, and hence the description thereof is omitted.

Next, a method of capturing the fundus image by using the OCT apparatus 200 of this embodiment is described.

The OCT apparatus 200 is capable of capturing the fundus image (see FIG. 2B) by using the camera portion 500.

In adjustment before imaging, the quick return mirror 318, similarly to the above-mentioned tomogram, is not set to be flipped up (solid line). The positional adjustment of the subject eye 107 before imaging the image is performed in the state where the halogen lamp 316 illuminates the retina 127 and the retina 127 is observed by the area sensor 321.

Appropriately, the fixation lamp 320 is used for urging the subject eye to be fixed for adjusting the position or the like of the subject eye 107 so that a desired part of the retina 127 can be observed.

When the adjustment is finished, the stroboscopic tube 314 is activated to emit light. At the same time, the quick return mirror 318 is flipped up, so that the fundus image is captured by using the camera portion 500 and is displayed.

Appropriately, positions of the fundus image and the tomogram 132 are associated with each other and are displayed by using the computer 125.

Embodiment 3

Embodiment 3 is characterized in wavelength characteristics of a dichroic mirror 405 and a method of adjusting an optical system, in a connection adapter in addition to Embodiment 2.

Other structures are the same as in Embodiment 2, and hence the description thereof is omitted.

A structure of an optical system of an OCT apparatus including the connection adapter according to this embodiment is described.

Figure 5A:
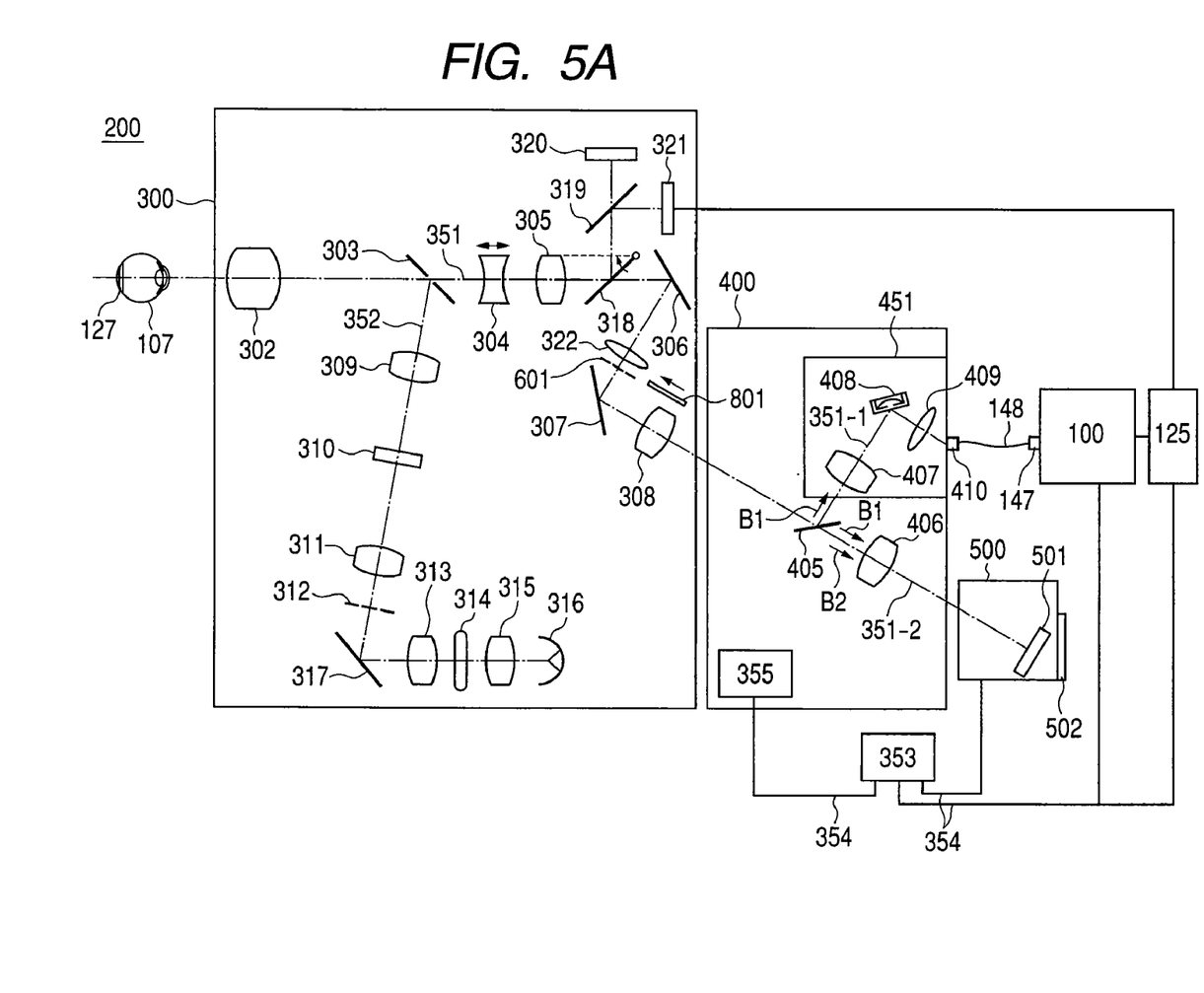
FIG. 5A is a diagram illustrating a structure of an optical system in an OCT apparatus according to Embodiment 3 of the present invention.

FIG. 5A is a diagram illustrating a structure of the optical system according to this embodiment.

In FIG. 5A, the same structure as in FIGS. 1A, 1B, 2A, 2B, 3, 4A, and 4B is denoted by the same reference numeral.

The OCT apparatus 200 of this embodiment is constituted so as to use an OCT imaging portion 100 and a camera portion 500 for capturing a tomographic image (OCT image) and a fundus image (plane image) of a retina 127 of a subject eye 107.

The structure of a fundus camera main body portion 300 is the same as in Embodiment 2, and hence the description thereof is omitted.

the above mentioned optical systems are configured in a manner that the fundus camera main body portion 300 is provided with a surface 601 that is conjugate with the fundus between the field lens 322 and the mirror 307, so that, with its structure, a chart 801 can be inserted in that position. However, being conjugate with the fundus is based on the premise that the fundus is of the subject eye that is a normal eye with 0 diopter.

This chart 801 is described later.

Next, the structure of the connection adapter 400 in this embodiment is described with reference to FIG. 5A.

The connection adapter 400 divides the optical path 351 into an optical path 351-1 for imaging the tomographic image and an optical path 351-2 for imaging the fundus image by a dichroic mirror 405 as a beam splitter. Note that the dichroic mirror 405 has characteristics to reflect most part of beams B1 for imaging the tomographic image and to transmit other small part of the same. In addition, the dichroic mirror 405 has characteristics to hardly lead beams B2 for imaging the fundus image to the optical path 351-1 for imaging the tomographic image. Specifically, the dichroic mirror 405 reflects most part of beams having wavelengths of 805 to 855 nm that are wavelengths of a light source 101 for imaging the tomographic image and transmits a small part of the same. The dichroic mirror 405 transmits substantially the entire beams in the visible wavelength range for imaging the fundus image and hardly reflects the same.

Here, the connection adapter 400 includes relay lenses 406 and 407, an XY scanner 408, and a collimate lens 409. The collimate lens 409 is capable of moving in the optical axis direction.

Here, the relay lens 406 is retained in a movable manner similarly to Embodiment 2, so that the optical axis of the optical path 351-2 can be adjusted by fine positional adjustment.

The XY scanner 408, the relay lens 407, the collimating lens 409, and the connector 410 constitute one unit 451. This unit 451 is set to be capable of moving with respect to the dichroic mirror 405 so that the optical axis of the optical path 351-1 can be adjusted.

In addition, in the camera portion 500, an area sensor 501 is disposed to have sensitivity to at least some of the wavelengths of the light source 101 for imaging the tomographic image. In addition, the camera portion 500 is provided with a display portion 502, which is capable of displaying an image that is projected onto the area sensor 501.

Here, adjustment of the optical path is described.

First, the optical path 351-2 of the camera portion 500 side is adjusted. The relay lens 406 is adjusted concerning a position in the optical axis direction and a position in the plane perpendicular to the optical axis, so that the fundus image can be imaged by the area sensor 501 correctly.

Figure 5B:
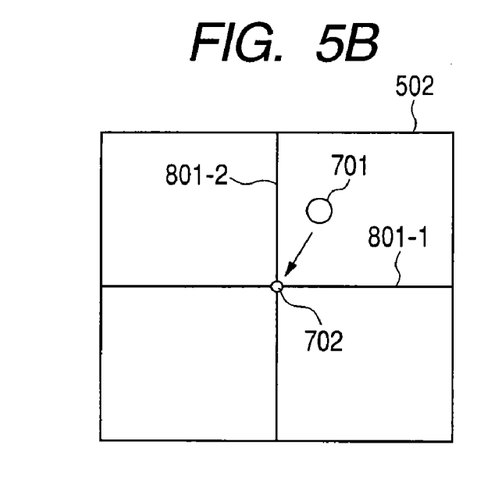
FIG. 5B is a diagram illustrating a display on a display portion when an optical axis adjustment is performed according to Embodiment 3 of the present invention.
Figure 5C:
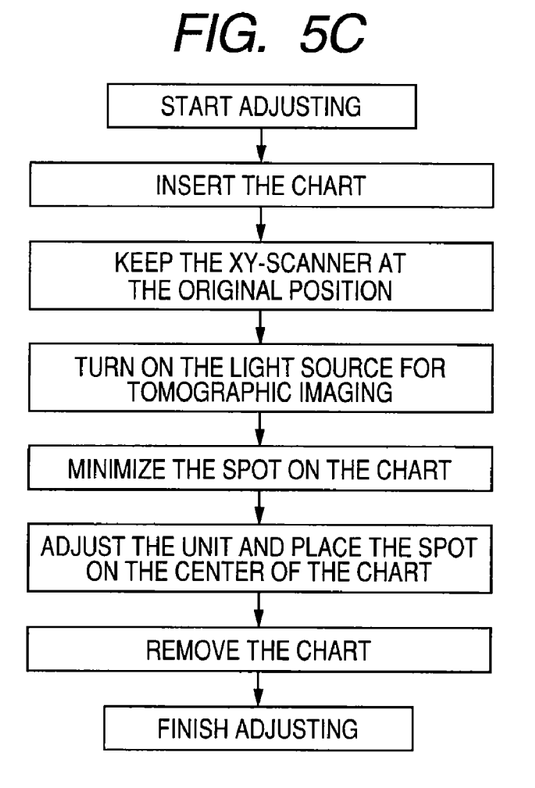
FIG. 5C is a diagram illustrating an adjustment step according to Embodiment 3 of the present invention.

Next, the optical path 351-1 of the tomographic imaging side is adjusted. FIG. 5C illustrates the adjustment procedure.

In the first step, the chart 801 is inserted in a fundus conjugate plane 601. The chart 801 has a glass plate on which lines are formed by vapor deposition of chrome. The intersection of the lines indicates the optical axis. In addition, when the chart 801 is inserted, the surface on which the lines are formed by vapor deposition corresponds to the fundus conjugate plane.

In the next step, the XY scanner 408 keeps each position of each reflecting surface at an original position as a center of a swing angle.

In the next step, the light source 101 is activated. The beams from the light source 101 are led to the connection adapter 400 via the connector 410 and reach the chart 801 via the optical path 351-1. A part of the beams from the light source 101, which is reflected by the chart 801, is led to the area sensor 501 in the camera portion 500 by the above-mentioned wavelength characteristics of the dichroic mirror 405. On the other hand, a visible light image of the chart 801 is also led to the area sensor 501. If necessary, the chart 801 is illuminated by beams including the visible light from the side of the fundus camera main body portion 300. FIG. 5B illustrates a screen when the display portion 502 provided in the camera portion 500 is adjusted as described above, which displays an image formed on the area sensor 501. Numerals 801-1 and 801-2 denote the visible light images of the chart 801, and numerals 701 and 702 denote images of the beams from the light source 101 before and after the adjustment, respectively. The optical system constituted of the relay lenses 308 and 406 is designed to have a aberration suppressed correctly not only for a wavelength in the visible light range for imaging the fundus image but also for a wavelength of beams for imaging the tomographic image. Therefore, no shift from the visible light or unsharpness is generated on the area sensor 501.

Numerals 701 and 702 actually indicate images of beams emission points on the end portion of the fiber 148 connected to the connector 410, and it is preferred that they be the smallest state on the chart 801 disposed on the fundus conjugate plane 601.

In the next step, the collimating lens 409 is moved in the optical axis direction while the image 701 before the adjustment is being viewed, so that the spot becomes minimized. The display portion 502 includes a function of enlarging the image, which is used if necessary.

In the next step, the unit 451 is moved in the plane perpendicular to the optical axis while the small spot is being viewed, so that the spot agrees with the center of the chart represented by 702.

In the next step, the chart 801 is removed and the adjustment is finished.

In the adjustment of this embodiment, the optical axis adjustment of the fundus camera main body portion 300 and the connection adapter 400 can be performed without using a special tool such as another optical system or another imaging system. In addition, the fundus conjugate plane is disposed in the fundus camera main body portion 300, so that the optical axis can be adjusted on the spot. Further, the optical system for imaging the tomographic image having a long optical path length to the fundus can also be adjusted easily.

A method of capturing the tomographic image and a method of capturing a fundus image are the same as in Embodiment 2, so the description thereof is omitted.

In the above description, the chart 801 is disposed in the fundus camera main body portion 300, but the chart 801 may be detachable so as to be attached only when the adjustment is performed.

In addition, the dichroic mirror 405 that is disposed as a beam splitter may be replaced with a half mirror. This half mirror reflects beams of a certain ratio of wide wavelength range and transmits the other beams. Therefore, it reflects the beams for imaging the tomographic image and the visible light for imaging the fundus image at substantially the same ratio and transmits the other parts. The visible light also enters the fiber 148 for imaging the tomographic image, but it is sufficient to dispose a member that substantially does not transmit the visible light between the half mirror and the balanced detector 122 in the tomographic imaging portion 100.

In addition, the adjustment is performed while the image displayed on the display portion 502 is being viewed, but it is possible to calculate an unsharpness of the spot from the image and a shift amount from the intersection on the chart by the computer 125 and to display them on the display portion 502 so that the adjustment of each portion is performed while that data is being viewed.

In addition, the display portion 502 is provided in the camera portion 500, but the display portion of the computer 125 may be used instead.

Other Embodiments

Aspects of the present invention can also be realized by a computer of a system or apparatus (or devices such as a CPU or an MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2008-273880, filed Oct. 24, 2008, and No. 2009-240891, filed Oct. 19, 2009, which are hereby incorporated by reference herein in their entirety.

What is claimed is:

1. An adapter configured to connect a fundus camera main body portion and a camera portion in a detachable manner, being disposed between the fundus camera main body portion and the camera portion so that the camera portion that images a surface image of a fundus as an object is attached to the fundus camera main body portion, wherein the fundus camera main body portion includes a quick return mirror, the adapter comprising:
   a first light guide unit configured to guide return beams guided from the fundus camera main body portion to a tomographic imaging portion for imaging the tomographic image; and
   a second light guide unit configured to guide return beams guided from the fundus camera main body portion to the camera portion for imaging the surface image of the fundus;
   a branching unit configured to branch an optical path of the return beams guided from the fundus camera main body portion into the first light guide unit and the second light guide unit;
   a scanning unit configured to scan measuring beams guided from the tomographic imaging portion, wherein the scanning unit is located in the first light guide unit; and
   a control unit configured to control the quick return mirror and the scanning unit.

2. The adapter according to claim 1, wherein the branching unit is a beam splitter which branches one of the tomographic image measuring beams and the fundus image measuring beams so as to guide the beams to the first light guide unit and the second light guide unit.

3. The adapter according to claim 2, wherein the beam splitter guides beams having some wavelengths of the tomographic image measuring beams to the second light guide unit.

4. The adapter according to claim 1, further comprising:
   a fixation lamp configured to make an eye as the object to gaze; and
   a quick return mirror provided in an optical path between the fixation lamp and one of the first light guide unit and the second light guide unit.

5. The adapter according to claim 1, further comprising:
   an area sensor configured to register an eye as the object; and
   a quick return mirror provided in an optical path between the area sensor and one of the first light guide unit and the second light guide unit,
   wherein image information captured by the area sensor may be delivered to an image display unit.

6. The adapter according to claim 1, further comprising at least one of:
   a position adjusting unit configured to adjust positions of the fundus camera main body portion and the adapter, respectively; and
   an optical axis adjusting unit configured to adjust a positional relationship between an optical axis of the fundus camera main body portion and an optical axis of the adapter.

7. An optical tomographic imaging apparatus configured to image a tomographic image of a fundus as an object, comprising:
   a fundus camera main body portion;
   a camera portion attached to the fundus camera main body portion configured to image a surface image of the fundus;
   a adapter according to claim 1 for connecting the fundus camera main body portion and the camera portion, being disposed between the fundus camera main body portion and the camera portion; and
   a tomographic imaging portion configured to image the tomographic image by the tomographic image measuring beams guided from the first light guide unit in the adapter.

8. A program stored on a non-transitory computer-readable storage medium for a computer of the optical tomographic imaging apparatus according to claim 7 to execute a imaging method of the optical tomographic imaging apparatus.

9. A non-transitory computer-readable storage medium storing the program according to claim 8, wherein the program is configured so as to be read out by the computer.

10. The optical tomographic imaging apparatus according to claim 7, wherein the fundus camera main body portion has a fundus conjugate plane that is substantially conjugate optically with the fundus position.

11. The optical tomographic imaging apparatus according to claim 10, wherein a chart that indicates the optical axis of the fundus camera main body portion can be inserted in the fundus conjugate plane.

12. The optical tomographic imaging apparatus according to claim 7, wherein the camera portion comprises an area sensor that is sensitive to at least some wavelengths of the tomographic image measuring beams.

13. An optical tomographic imaging apparatus configured to image a tomographic image of a fundus as an object, comprising:
   a fundus camera main body portion configured to image a surface image of a fundus of an eye as the object and including a quick return mirror;
   a tomographic imaging portion configured to image a tomographic image of the eye as the object;
   a branching unit configured to branch an optical path of the tomographic imaging portion from the optical path of the fundus camera main body portion;
   a scanning unit configured to scan measuring beams guided from the tomographic imaging portion;
   a controlling unit configured to control the quick return mirror and the scanning unit; and
   a chart, detachably attached to the fundus camera main body portion, that indicates an optical axis of the fundus camera main body portion, which is provided in a position substantially conjugate optically with a fundus position, and which is made of a material that reflects light guided to the tomographic imaging portion configured to image the tomographic image.

14. An adapter that is detachable from a fundus camera main body portion which is configured to image a surface image of a fundus as an object, the adapter comprising:
   a branching unit configured to branch an optical path guided to a tomographic imaging portion configured to image a tomographic image of an eye as the object;
   a scanning unit configured to scan measuring beams guided from the tomographic imaging portion; and
   a controlling unit configured to control a quick return mirror that is provided in an optical path of the fundus camera main body portion in a detachable manner, and to control the scanning unit, wherein the scanning unit is configured to scan the measuring beam in a state where the quick return mirror is flipped up from the optical path of the fundus camera main body portion.

15. The adapter according to claim 14, wherein, when the quick return mirror is flipped up from the optical path of the fundus camera main body portion, the measuring beams scanned by the scanning unit are guided to the eye as the object via the branching unit, and the tomographic imaging portion images the tomographic image.

16. The adapter according to claim 14, wherein, when the quick return mirror is flipped down on the optical path of the fundus camera main body portion, the quick return mirror reflects visible light guided from a fixation lamp included in the fundus camera main body portion.

17. The adapter according to claim 14, further comprising:

an area sensor configured to register the eye as the object, which uses a part of infrared light reflected by the quick return mirror, when the quick return mirror is flipped down on the optical path of the fundus camera main body portion.

18. An optical tomographic imaging apparatus comprising:

a fundus camera main body portion configured to image a surface imaging of a fundus image of an eye as an object;

a quick return mirror provided in an optical path of the fundus camera main body portion;

a tomographic imaging portion configured to image an tomographic imaging of the eye as the object;

a branching unit configured to branch an optical path of the tomographic imaging portion from the optical path of the fundus camera main body portion;

a scanning unit configured to scan measuring beams guided from the tomographic imaging portion; and a controlling unit configured to control the quick return mirror and the scanning unit, wherein the scanning unit is further configured to scan the measuring beams in a state where the quick return mirror is flipped up from the optical path of the fundus camera main body portion.

19. The optical tomographic imaging apparatus according to claim 18, wherein, when the quick return mirror is flipped up from the optical path of the fundus camera main body portion, the measuring beam scanned by the scanning unit is guided to the eye as the object via the branching unit, and the tomographic imaging portion images the tomographic imaging of the eye as the object.

20. The optical tomographic imaging apparatus according to claim 18, wherein, when the quick return mirror is flipped down on the optical path of the fundus camera main body portion, the quick return mirror reflects visible light guided from a fixation lamp included in the fundus camera main body portion.

* * * * *